(12) United States Patent
Bettle, III

(10) Patent No.: US 9,393,283 B2
(45) Date of Patent: Jul. 19, 2016

(54) POVIDONE-IODINE TOPICAL COMPOSITION

(71) Applicant: Microdermis Corporation, Princeton, NJ (US)

(72) Inventor: Griscom Bettle, III, Sarasota, FL (US)

(73) Assignee: Microdemis Corporation, Princeton, NJ (US)

( * ) Notice: Subject to any disclaimer, the term of this patent is extended or adjusted under 35 U.S.C. 154(b) by 0 days.

(21) Appl. No.: 13/916,882

(22) Filed: Jun. 13, 2013

(65) Prior Publication Data

US 2014/0093583 A1    Apr. 3, 2014

Related U.S. Application Data

(63) Continuation of application No. 13/696,385, filed as application No. PCT/US2011/035309 on May 5, 2011, now abandoned.

(60) Provisional application No. 61/332,417, filed on May 7, 2010.

(51) Int. Cl.

| | | |
|---|---|---|
| *A61K 36/889* | (2006.01) | |
| *A61K 36/185* | (2006.01) | |
| *A61K 9/00* | (2006.01) | |
| *A61K 31/165* | (2006.01) | |
| *A61K 33/18* | (2006.01) | |
| *A61K 31/4015* | (2006.01) | |
| *A61K 35/644* | (2015.01) | |

(52) U.S. Cl.
CPC .............. *A61K 36/889* (2013.01); *A61K 9/0014* (2013.01); *A61K 31/165* (2013.01); *A61K 31/4015* (2013.01); *A61K 33/18* (2013.01); *A61K 35/644* (2013.01)

(58) Field of Classification Search
None
See application file for complete search history.

(56) References Cited

U.S. PATENT DOCUMENTS

| | | | |
|---|---|---|---|
| 4,839,080 A * | 6/1989 | Jungermann et al. | 510/131 |
| 5,716,611 A * | 2/1998 | Oshlack et al. | 424/78.25 |
| 6,221,346 B1 * | 4/2001 | Streels | 424/69 |
| 6,583,184 B1 | 6/2003 | Duggan | |
| 6,878,378 B1 | 4/2005 | Yamaki et al. | |
| 2004/0122105 A1* | 6/2004 | Bettle et al. | 514/625 |
| 2004/0122115 A1 | 6/2004 | Espinoza et al. | |
| 2009/0226541 A1 | 9/2009 | Scholz et al. | |
| 2010/0092413 A1* | 4/2010 | Bellman | 424/59 |

FOREIGN PATENT DOCUMENTS

EP    0 742 006 A1    11/1996

OTHER PUBLICATIONS

Extended European Search Report for EP11778327.4, 6 pages (Oct. 10, 2013).
International Search Report for PCT/US2011/035309, 4 pages (Feb. 9, 2012).
No Author Listed, Betaisodona Salbe, Rote Liste Service GmbH: "Rote Liste", Frankfurt am Main, paragraph 85013 (2007).
Pittet, D., Improving compliance with hand hygiene in hospitals, Infection Control and Hospital Epidemiology, 21(6):381-386 (2000).
Written Opinion for PCT/US2011/035309, 5 pages (Feb. 9, 2012).

* cited by examiner

*Primary Examiner* — Chris R Tate
*Assistant Examiner* — Randall Winston
(74) *Attorney, Agent, or Firm* — Choate, Hall & Stewart LLP; Brenda Herschbach Jarrell; Su Kyung Suh

(57) ABSTRACT

The present invention relates to a topical pharmaceutical composition comprising povidone-iodine, a tertiary amide, surfactant and coconut oil, useful for killing microbes and treating wounds or sores on the surface of the skin.

16 Claims, No Drawings

POVIDONE-IODINE TOPICAL COMPOSITION

RELATED APPLICATION

The present application is claiming priority of U.S. Ser. No. 61/332,417 filed on May 7, 2010 in the USPTO.

FIELD OF THE INVENTION

The present invention is directed to a topical composition comprised of povidone-iodine as an antiseptic.

BACKGROUND

A hospital acquired infection (HAI) is a very serious problem in the United States and worldwide. Current estimates are that 99,000 people die annually in the U.S. from these infections. An important and rapidly emerging HAI is *Clostridium difficile* (*C. diff.*). In 2008, the Association for Professionals in Infection Control and Epidemiology (APIC) performed the largest and most comprehensive study of *Clostridium difficile* rates to date which demonstrated the severity of this problem. This study was a survey of 12.5% of acute care hospitals in the United States, and it found that 13 of every 1000 hospitalized patients were infected or colonized with *C. diff.* (94.4% were infected). This was 6.5 to 20 times higher than previous estimates because those studies were limited in scope. Of those patients infected, 72.5% were considered to be HAI's. In addition to its increasing presence, *C. diff.* infections are becoming more virulent; the mortality rate has increased from 1.2% in 2000 to 2.2% in 2004. The incidence of deaths from *C. diff.* was greater than the incidence of infections from all other intestinal infections combined. The cost of treating these infections in the US is staggering and is estimated to be $17.6 million to $51.1 million per day, with some estimates indicating an annual cost in the U.S. of $1 billion to $3.2 billion. There are also additional costs incurred outside of healthcare facilities that were not included in these estimates, such as lost productivity, pain and suffering of the patients and the time that medical professionals spend treating them, making this a multibillion dollar healthcare problem.

*C. diff.* infections are also becoming more aggressive as evidenced by the increasing mortality rate from this infection which was 1.2% in 2000 and 2.2% in 2004. This is most likely due to the emergence of a new strain of *C. diff.*, termed ribotype 027, which is now the most virulent and common cause of infectious diarrhea in hospitals and long term care facilities in the United States, Europe and Japan. Its increased virulence is due to the production of twenty times more of the two main *C. diff.* toxins and one additional toxin which produce increased damage of the colonic mucosa and increased episodes of sepsis. This strain of *C. diff.* is also more resistant to standard therapy and more likely to relapse than any other present strain.

Numerous studies and historical information support the fact that the majority of *C. diff.* infections and other HAI's result from poor adherence to proper hand hygiene by healthcare personnel. Studies have shown that 60% of physicians and nurses caring for *C. diff.* infected patients from their hands. Poor hand hygiene and unreliable activity of hand sanitizers against *C. diff.* have resulted in the rapid growth and widespread occurrence of healthcare associated diarrhea caused by this organism which creates significantly negative health impacts on patients and staff. The rapid growth of *C. diff.* infections has earned it the recent distinction as "the new superbug on the rise in hospitals." Poor hand hygiene is a major challenge in controlling the spread of *C. diff.* infections because no currently available hand sanitizers are active against it or any other spore forming bacteria.

There is an obvious need for an effective hand hygiene strategy that can evaluate the rapidly emerging problem and at the same time promote hand hygiene compliance among healthcare personnel.

There are many anti-microbials on the market which can potentially be used to combat this and other microbes. One such drug is polyvinylpyrrolidone complexed with iodine, which is widely recognized for its anti-microbial properties. This complex is also widely known as povidone-iodine. Since the iodine is tightly complexed, germicidal properties can be obtained without the toxicity or staining concerns associated with compositions containing elemental iodine. Its use in medicine and veterinary medicine as an anti-infective is widely recognized. Products with 5-10% povidone-iodine are over the counter drugs.

Unfortunately povidone-iodine complexes have a short shelf-life, as the iodine chemically decays. U.S. Patent Application No. 2004/0122105 which discloses in Example 33 thereof a povidone-iodine complex containing a tertiary amide, EDTA, PCA, TEA, lauricidin, beeswax, dimethicone, Triton X-100, Nonoxynol-9, Merquat 550, Merguard 1200, propolis, propylene glycol, chlorohexidine gluconate solution, and Carbomer 940 NF, and a final pH of the composition being 4.4, has a shelf life of about 12 months.

Another iodine-povidone product, called Microdine, manufactured by Microorganics LLC, has a pH of 3.6 and a shelf life of 16 months.

But, an antiseptic crème distributed nationwide requires a long shelf-life. A 12-month shelf life is only marginally acceptable. An 18-month shelf life or even better, a 24 month shelf life is preferable.

The present invention is directed to a povidone-iodine formulation that overcomes the aforesaid problems and has a long shelf life.

SUMMARY OF THE INVENTION

An aspect of the present invention is directed to a topical pharmaceutical composition comprising povidone-iodine, in anti-septive effective amounts, a tertiary amide or salt thereof or a hydrate thereof in film forming effective amounts, at least one surfactant, for example at least one non-ionic surfactant or at least one cationic surfactant or a combination of at least one cationic surfactant and one non-ionic surfactant, the surfactant or surfactants being present in emulsifying effective amounts, and coconut oil, said composition having a pH of less than about 3.5 and a specific gravity of greater than about 0.9.

In an embodiment, the present invention is directed to a topical pharmaceutical composition comprising an antiseptic effective amount of a povidone-iodine complex, wherein the amount of complexed iodine in the povidone-complex ranges from about 4% to about 12% by weight of the povidone-iodine complex, a tertiary amide in an amount ranging from about 0.1% to about 2% of the pharmaceutical composition, coconut oil in an amount ranging from about 0.8% to about 2% of the pharmaceutical composition, and at least one surfactant present in an emulsifying effective amounts, said composition having a pH of about 2.0 to about 3.5 and having a specific gravity ranging from about 0.9 to about 1.1. In an embodiment, the surfactant is a non-ionic surfactant, and in another embodiment, it is a cationic surfactant, e.g., a quaternary ammonium cation (hereinafter a "quaternary cationic surfactant) and in another embodiment, a mixture of a nonionic surfactant and a quaternary cationic surfactant. In accordance with this invention, the pharmaceutical composition has a shelf-life of at least about 24 months.

Another aspect of the present invention is directed to removing microbes from the hands of a subject which comprises placing a microbicidal effective amount of the pharmaceutical composition on at least one of the hands of a subject, and thoroughly rubbing the composition in the hands together to cover the entire surface of the skin of both hands with said composition, allowing the composition to remain on the surface of the skin on the hands for sufficient time to kill the microbes thereon and rinsing the pharmaceutical composition off the hands with water.

Another aspect of the invention is directed to removing microbes from the skin of a subject which comprises placing a microbicidal effective amount of the pharmaceutical composition on the area of the skin of the subject to be cleansed; thoroughly rubbing the pharmaceutical composition on said area of the skin to completely cover the area of the skin to be cleansed with the pharmaceutical composition, allowing the pharmaceutical composition to remain on the surface of the area of the skin for a time sufficient to kill the microbes thereon and rinsing the pharmaceutical composition off of the area of the skin with water.

Another aspect of the present invention is directed to a method of decreasing the probability that a subject will contract HAI on a particular area of the body, which comprises (a) placing a microbicidal effective amount of the pharmaceutical composition on the area of the skin to be cleansed of microbes; (b) thoroughly rubbing the pharmaceutical composition on this skin area so that it is completely covered with said composition, (c); allowing the composition to remain on the surface of the skin for a time sufficient to kill the microbes thereon; (d) rinsing the pharmaceutical composition off the area of the skin to be cleansed of microbes with water, and (e) repeating these process steps (a)-(d) at least once about every six hours. For example, if the area of the skin to be cleansed of microbes is the hands of a subject, the process comprises placing a microbicidal effective amount of the pharmaceutical composition on at least one hand; thoroughly rubbing the hands together to completely cover the hands including all of the fingers, with said composition; and permitting the composition to remain on the hands for sufficient time to kill the microbes thereon; rinsing the composition off the hands with water and repeating these steps at least once about every six hours.

Another aspect of the present invention is directed to treating an open wound or sore on the skin of a subject which comprises placing a microbicidal effective amount of the pharmaceutical composition onto the wound or sore and rubbing the composition thoroughly thereon.

DETAILED DESCRIPTION OF THE INVENTION

The pharmaceutical composition of the present invention is effective in killing various microbes, including bacteria, viruses, molds, fungus and protozoas. For example, it is effective in killing C. diff. If the subject, including hospital workers and/or patients utilizes the pharmaceutical composition of the present invention in accordance with the procedure described herein, the incidence of HAI will be dramatically reduced.

The pharmaceutical composition of the present invention is quite stable, having a shelf-life for at least about 24 months. The present inventor has found that the shelf-life can be increased when the pH is lowered. However, the lowering of the pH on previous compositions in the art comprised of povidone iodine, such as the Microdine composition, fell apart when the pH was lowered. As a result, the present inventor had to find a different formulation to increase the shelf life of the povidone-iodine composition. For example, the use of coconut oil and the removal of certain components in Microdine made it possible to lower the pH and yet maintain the integrity of the composition.

An essential element of the present composition is povidone-iodine. Povidone-iodine is a stable chemical complex of polyvinylpyrollidone and elemental iodine. It is commercially available and contains from about 8.0% to about 12% complexed (available) iodine in the dry povidone-iodine complex. In another embodiment, the povidone-iodine has about 9 to about 11% available (complexed) iodine in the povidone-iodine complex. It exhibits a broad range of microbicidal activity against bacteria, fungi, protozoa and viruses and mold. It is present in the current composition in amounts effective to kill microbes, e.g., bacteria, mold, fungus, viruses and protozoas. In an embodiment, it is present in an amount ranging from about 1 to about 40% by weight of the pharmaceutical composition; and in another embodiment, it is present in an amount ranging from about 3% to about 20% by weight of the pharmaceutical composition and in another embodiment, it is present in an amount ranging from about 5% to about 10% by weight of the pharmaceutical composition. It is to be noted, as used herein, the term "povidone-iodine" refers to the iodine complexed with povidone when it is first prepared. It does not include any free povidone, i.e., povidone that is not complexed with iodine. Povidone that is not complexed with iodine may be additionally present in the instant composition.

A second component of the present composition is a tertiary amide or salt of the tertiary amide or a hydrate of the tertiary amide, said tertiary amide having the formula:

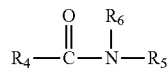

wherein
$R_4$ is a saturated fatty group having 11-29 carbon atoms;
$R_5$ and $R_6$ are independently lower alkyl, aryl, aryl lower alkyl or saturated fatty group of 11-29 carbon atoms or $R_7$;
$R_7$ is $-R_1-Ar-O-R_2-O-R_3$;
$R_1$ is alkyl group containing 1-15 carbon atoms;
$R_2$ and $R_3$ are independently lower alkyl groups containing 1-6 carbon atoms and Ar is aryl.

The term "lower alkyl", when used alone or in combination, means an alkyl group containing 1-6 carbon atoms. The lower alkyl group may be branched or straight chained. Preferred lower alkyl contains 1-4 carbon atoms and more preferably 1 or 2 carbon atoms. Examples of lower alkyl include methyl, ethyl, propyl, isopropyl, butyl, t-butyl, isobutyl, sec-butyl, pentyl and hexyl.

As used herein, the term "aryl", when used alone or in combination, is an aromatic group comprised solely of carbon ring atoms. The aryl group may be monocyclic, bicyclic or tricyclic. If more than 1 ring is present, the rings are fused; thus the aryl group also includes polynuclear aromatics, i.e., bicyclic and tricyclic fused aromatic rings. The aryl group contains 4n+2 ring carbon atoms, wherein n is 1-4. The aryl group contains 6, 10, 14 or 18 ring carbon atoms and up to a total of 25 carbon atoms. It is preferred that n is 1-3. In an embodiment, aryl groups are phenyl, naphthalene, including alpha and beta-naphthalene, anthracene, phenanthrene, and the like. In another embodiment the aryl group is naphthalene or phenyl, and in still another embodiment, the aryl group is phenyl.

The aryl group may be unsubstituted or substituted with one or more electron donating groups or electron withdrawing groups. The terms "electron withdrawing groups" and "electron donating groups" refer to the ability of a substitutent to withdraw or donate electrons relative to that of hydrogen if the hydrogen atom occupied the same position in the molecule. These terms are well understood by one skilled in the art and are discussed in Advanced Organic Chemistry, by J. March, 4$^{th}$ Ed. John Wiley and Sons, New York, N.Y. pp. 16-18 (1992), and the discussion therein is incorporated by reference. Examples of electron withdrawing groups include halo, especially fluoro, bromo, chloro, iodo, and the like; nitro; carboxy; formyl; lower alkanoyl; carboxyamido; triloweralkylamino; aryl; trifluoromethyl; aryl lower alkanoyl; lower carbalkoxy; and the like. Examples of electron donating groups include such groups as hydroxy; lower alkoxy, including methoxy, ethoxy, and the like; lower alkyl; amino; lower alkylamino; dilowerlakylamino; aryloxy (such as phenoxy); mercapto; mercapto lower alkyl; lower alkylthio; and the like. One skilled in the art will appreciate that the aforesaid substituents may have electron donating properties under one set of circumstances and electron withdrawing properties under different chemical conditions or circumstances; these are also contemplated to be within the scope of these terms. Moreover, the present invention contemplates any combination of substituents selected from the above-identified terms.

In an embodiment, the aryl group is unsubstituted or substituted by lower alkyl groups.

The term "aryl lower alkyl group" refers to a lower alkyl group as defined herein bridging an aryl group, as defined herein, to the main chain. Examples include benzyl, phenethyl, phenpropyl, phenisopropyl, phenbutyl, diphenyl methyl, 1,1-diphenylethyl, 1,2-diphenylethyl, and the like.

The fatty acid or fatty alcohol, as used herein, is a saturated aliphatic which may be straight or branched chain. It is preferred that the fatty acid contains 12-30 carbon atoms and more preferably 16-22 carbon atoms and most preferably 16-20 carbon atoms. Examples include lauric acid, myristic acid, palmitic acid, stearic acid, behenic acid, arachidic acid, and the like.

As used herein, the term "fatty group", when used alone or in combination is a fatty acid group without the terminal carboxy moiety on the omega carbon of the chain.

In other words, it is $R_8$ wherein

is the corresponding fatty acid. The fatty group ($R_8$) contains 11-29 carbon atoms and more preferably contains an odd number of carbon atoms. In an embodiment, it contains 15-21 carbon atoms. All of the carbon-carbon bonds in $R_8$ are saturated. It may be straight chained or branched.

In an embodiment, the tertiary amides used have the formula

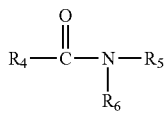

or pharmaceutically acceptable salts thereof wherein $R_5$ and $R_6$ are independently aryl, aryl lower alkyl, a saturated fatty group containing 11-29 carbon atoms, or $R_7$;

$R_4$ is a saturated fatty group containing 11-29 carbon atoms, and $R_7$ is

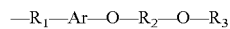

wherein $R_2$ and $R_3$ are lower alkyl groups containing 1-6 carbon atoms, $R_1$ is a lower alkyl group and Ar is aryl.

These tertiary amides and hydrates are described in U.S. Patent Publication No. 2004/0122105, the contents of which are incorporated by reference. However, it is to be understood that the tertiary amide or hydrate cannot have any groups thereon that can react with free iodine, such as carbon-carbon double bonds unless they are part of an aromatic ring, as described herein.

The $R_4$ in an embodiment is an aliphatic containing 15-21 carbon atoms. The $R_4$ group is completely saturated.

In an embodiment $R_2$ and $R_3$ contains 1-3 carbon atoms and more preferably 1 or 2 carbon atoms. It is also preferred that $R_2$ and $R_3$ are the same. It is even more preferred that $R_2$ and $R_3$ are the same and contain 1 or 2 carbon atoms and most especially 2 carbon atoms. In an embodiment aryl is phenyl.

In an embodiment $R_7$ is

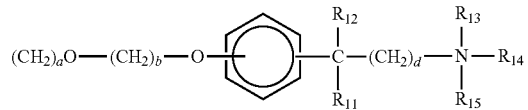

wherein $R_{11}$, $R_{12}$, $R_{13}$, $R_{14}$, $R_{15}$ are independently lower alkyl and a, b, d are independently 1-5.

In an embodiment, $R_{11}$ and $R_{12}$ are the same and $R_{13}$, $R_{14}$ and $R_{15}$ are the same. In another embodiment, $R_{12}$, $R_{11}$, $R_{13}$, $R_{14}$ and $R_{15}$ are the same.

In another embodiment, a, b and d are independently 1-3. In another embodiment, a and b are the same. In a still another embodiment a is 2, b is 3 and d is 1.

In another embodiment $R_7$ is

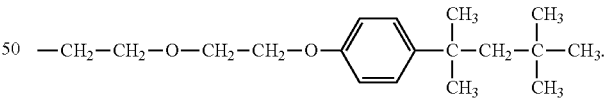

$R_1$ is, in an embodiment, an alkyl group containing 1-10 carbon atoms and in another embodiment containing 1-6 carbon atoms. It may be straight chained or branched.

In still another embodiment, $R_5$ and $R_6$ are both independently saturated fatty groups or one of $R_5$ and $R_6$ is an aryl or aryl lower alkyl and the other is $R_7$ or one of $R_5$ and $R_6$ is a saturated fatty group and the other is $R_7$, or one of $R_5$ and $R_6$ is a saturated fatty group and the other is an aryl or aryl lower alkyl.

In an embodiment, the tertiary amide is benzethonium stearamide or benzalkonium stearamide, i.e., compounds having the formula respectively,

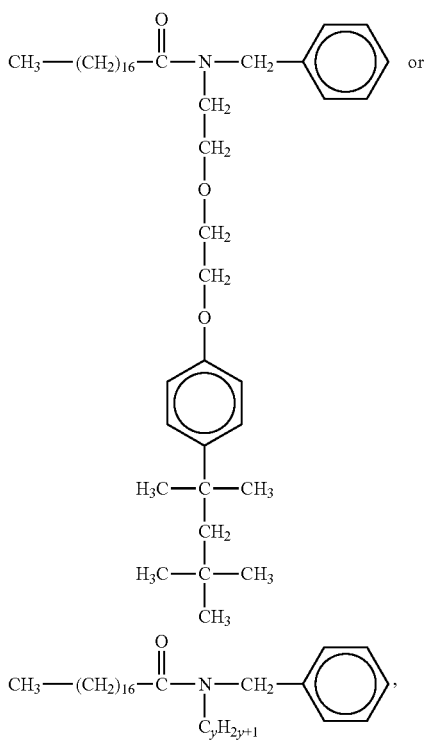

wherein y is 8, 10, 12, 14, 16, or 18.

In an embodiment y is 12 or 14.

In another embodiment the second component is a mixture of one or more tertiary amides or one or more tertiary amide hydrates or one or more salts of either or a combination thereof.

The second component, the tertiary amide or salt thereof or the tertiary amide hydrate or salts thereof are present in an amount effective to form a film over the area of the skin to be treated, as described below. In an embodiment, the second component is present in an amount ranging from about 0.1% to about 2% by weight of the pharmaceutical composition and in another embodiment, from about 0.5% to about 1.5% by weight of the pharmaceutical composition.

Another component of the composition is coconut oil or the triglycerides comprising the coconut oil, as described hereinbelow. Coconut oil is the oil extracted from the kernel or meat of matured coconut harvested from the coconut palm. It contains triglycerides which are made from various fatty acids. It contains about 45.1 to about 53.2% by weight lauric acid, about 16.8 to about 21.0% by weight myristic acid, about 7.5% to about 10% by weight palmitic acid, about 4.6 to about 10% by weight caprylic acid, about 0.4 to about 0.6% by weight caproic acid, about 5.0 to about 8.0% by weight capric acid, about 2.0 to about 4.0% by weight stearic acid, about 5.0 to about 10.0% by weight oleic acid and about 1.0 to about 2.5% by weight linoleic acid. The preferred coconut oil is virgin coconut oil obtained by grating the coconut and extracting the coconut milk and letting the coconut oil to separate naturally. Distributors include Tropical Traditions. In this embodiment, the coconut oil is unrefined. Virgin coconut oil is not refined, bleached or deodorized. It contains about 13.5% by weight $C_{8+10}$, about 44.6% by weight $C_{12}$, about 11% by weight $C_{16+18}$ fatty acids, with the remaining about 30% by weight containing $C_{14}$ and $C_{20}$ fatty acid.

Another source of coconut oil is hydrogenated coconut oil, which hydrogenates the carbon-carbon double bonds to substantially remove most of the unsaturation (carbon-carbon double bonds). Regardless, of the type of coconut oil utilized the amount of carbon-carbon double bonds present in the coconut oil is less than about 10% by weight.

In addition, besides virgin coconut oil, extra virgin coconut oil can be used, which in addition contain anti-oxidants.

The coconut oil is present in an amount greater than about 0.5% by weight of the pharmaceutical composition. In an embodiment, it is present in an amount ranging from about 0.5% to about 2% by weight of the composition, and in another embodiment, it is present in an amount ranging from about 0.6% to about 1.8% by weight of the composition, and in another embodiment, it is present in an amount ranging from about 0.75% to about 1.5% by weight and in another embodiment about 0.90 to about 1.2% by weight of the composition and in another embodiment, about 1% by weight of the composition.

Alternatively, the composition can contain a mixture of triglycerides, in which it contains about 40% to 50% by weight of triglycerides of $C_{12}$ fatty acids, about 5% to about 11% by weight of triglycerides of $C_8$ to $C_{10}$ fatty acids and about 10% to about 15% triglycerides of $C_{16}$+18 fatty acids and the remainder being triglycerides of fatty acids of one or more of $C_8$, C14 and $C_{20}$ fatty acids.

Another component of the composition is the surfactant(s). The composition can contain one surfactant or a combination of two or more surfactants. The surfactant can be an anionic surfactant, a cationic surfactant, an amphoteric surfactant or a non-ionic surfactant or a combination thereof of two or more surfactants in the same class or in different classes.

Examples of anionic surfactants include fatty acid soaps (e.g., sodium laurate, TEA stearate, sodium palmitate and the like); higher alkyl sulfates (e.g., sodium lauryl sulfate, potassium lauryl sulfate and the like); alkyl ether sulfates (e.g., triethanolamine POE-lauryl sulfate, sodium POE lauryl sulfate and the like); N-acylsarcosinic acids (e.g., sodium lauroylsarcosinate and the like); higher fatty acid amide sulfates (e.g., sodium N-myristoyl-N-methyltaurate, sodium cocoyl methyltaurate, sodium lauroyl methyltaurate and the like); phosphates (sodium POE oleyl ether phosphate, POE-stearyl ether phosphoric acid and the like); sulfosuccinates (e.g., sodium di-2-ethylhexylsulfosuccinate, sodium monolauroyl monoethanolamide polyoxyethylenesulfosuccinate, sodium lauryl polypropyleneglycol sulfosuccinate and the like); alkylbenzenesulfonates (e.g., sodium linear dodecylbenzenesulfonate, triethanolamine linear dodecylbenzenesulfonate, linear dodecylbenzenesulfonic acid and the like); higher fatty acid ester sulfates (e.g., sodium hydrogenated cocoglyceride sulfate and the like); N-acylglutamates (e.g., monosodium N-lauroylglutamate, disodium N-stearoylglutamate, monosodium N-myristoyl-L-glutamate and the like); sulfated oils (e.g., turkey red oil and the like); POE alkyl ether carboxylic acids; POE alkyl allyl ether carboxylates; alpha-olefinsulfonates; higher fatty acid ester sulfonates; secondary alcohol sulfates; higher fatty acid alkylolamide sulfate; sodium lauroyl monoethanolamide succinate; ditriethanolamine N-palmitoylaspartate; sodium caseinate and the like.

Examples of cationic surfactants include alkyl trimethyl ammonium salts (e.g., stearyl trimethyl anunonium chloride, lauryl trimethyl ammonium chloride and the like); alkyl pyridinium salts (e.g., cetylpyridinium chloride and the like); distearyl dimethyl ammonium chloride; poly(N,N-dimethyl-3,5-methylenepiperidinium)chloride; alkyl quaternary ammonium salts; alkyl dimethyl benzyl ammonium salts; alkylisoquinolinium salts; dialkylmorphonium salts; POE alkylamines; alkylamine salts; polyamine fatty acid derivatives; amyl alcohol fatty acid derivatives; benzalkonium chloride; benzethonium chloride and the like.

Examples of amphoteric surfactants include imidazoline series amphoteric surfactants (e.g., 2-undecyl-N,N,N-(hydroxyethylcarboxymethyl)-2-imidazoline sodium, 2-cocoyl-2-imidazolinium hydroxide-1-carboxyethyloxy disodium salt and the like); betaine series surfactants (e.g., 2-heptadecyl-N-carboxymethyl-N-hydroxyethylimidazolinium betaine, lauryldimethylaminoacetic acid betaine, alkylbetaine, amidebetaine, sulfobetaine and the like) and the like.

Examples of lipophilic nonionic surfactants include sorbitan fatty acid esters (e.g., sorbitan monooleate, sorbitan monoisostearate, sorbitan monolaurate, sorbitan monopalmitate, sorbitan monostearate, penta-2-ethylhexylic acid diglycerol sorbitan, tetra-2-ethylhexylic acid diglycerol sorbitan and the like); glycerin polyglycerin fatty acids (e.g., monocottonseed oil fatty acid glycerin, monostearic acid glycerin, monostearic acid glycerin malic acid and the like); propylene glycol fatty acid esters (e.g., monostearic acid propylene glycol and the like); hydrogenated castor oil derivatives; glycerin alkyl ethers and the like.

Examples of hydrophilic nonionic surfactants include POB-sorbitan fatty acid esters (e.g., POE-sorbitan monostearate, POE-sorbitan monooleate, POB-sorbitan tetraoleate and the like); POE-sorbit fatty acid esters (e.g., POE-sorbitol monolaurate, POE-sorbitol monostearate and the like); POE-glycerin fatty acid esters (e.g., POE-glyceryl monostearate, POE-glyceryl monoisostearate, and POE-glyceryl triisostearate); POE-fatty acid esters (e.g., POE-distearate, ethylene glycol distearate and the like); POE-alkyl ethers (e.g., POE-lauryl ether, POE-stearyl ether, POE-behenyl ether, POE-2-octyldodecyl ether, POE-cholestanol ether and the like); Pluronic type surfactants (e.g., Pluronic and the like); POE.POP-alkyl ethers (e.g., POE.POP-cetyl ether, POE.POP-2-decyltetradecyl ether, POE.POP-monobutyl ether, POE.POP-hydrogenated lanolin, POE.POP-glyceryl ether and the like); fused tetraPOE.tetraPOP-ethylenediamines (e.g., Tetronic and the like); alkanolamides (e.g., coconut oil fatty acid diethanolamide, lauric acid monoethanolamide, fatty acid isopropanolamide and the like); POE-propylene glycol fatty acid esters; POE-alkylamines; POE-fatty acid amides; sucrose fatty acid esters; alkylethoxydimethylamine oxides; trioleylphosphoric acid and the like. POE, hereinabove, is polyoxyethylene.

In an embodiment, the composition contains non-ionic surfactants and quaternary cationic surfactants. Examples include Triton-X-100, Nonoxynol NP-9, Arosurf TA-100 or a combination of two or all three, and the like.

The composition may contain 1 surfactant or a combination of surfactants. The surfactant(s) are present in an emulsifying effective amount. In an embodiment, the surfactants to present in total in an amount ranging from about 2% to about 10% by weight and in another embodiment, from about 5% to about 8% by weight of the pharmaceutical composition and most preferably from 6.5% to 7.5%, The pharmaceutical composition is prepared by incorporating the aforementioned ingredients into a known base for a topical composition for skin. The pharmaceutical composition is mixed with the ingredients normally used in a cosmetic or medical topical composition, according to the conventional methods. Examples of ingredients normally found include powders, lipid fat or oil, solid fats or oil, waxes, hydrocarbons, higher fatty acids, higher alcohols, esters, additional surfactants, water-soluble polymers, thickeners, film forming agents, ultraviolet absorbing agents, metal ion sequestering agents, lower alcohols, multivalent alcohols, pH adjusting agents, water, skin softeners, skin humectants and the like.

The composition may additionally contain a skin softener. Examples include allantoin, and comfrey extract (See U.S. Pat. No. 6,583,184) and water lily extracts (See U.S. Pat. No. 6,878,378) and the like. If present, it is present in skin softening effective amounts. In an embodiment, it is present in an amount ranging from about 0.5% to about 10% by weight of the pharmaceutical composition and in another embodiment, it is present in about 1% to about 3% by weight of the composition.

Examples of powders include inorganic powders, e.g., talc, kaolin, mica, sericite, muscovite, phlogopite, synthetic mica, red mica, biotite, vermiculite, magnesium carbonate, calcium carbonate, aluminum silicate, barium silicate, calcium silicate, magnesium silicate, strontium silicate, tungsten acid metal salt, magnesium, silica, zeolite, barium sulfate, calcinated calcium sulfate (calcined gypsum), calcium phosphate, fluorine apatite, hydroxyapatite, ceramic powder, metal soap (e.g., zinc myristate, calcium palmitate, aluminium stearate), boron nitride and the like); organic powders, e.g., polyamideresin powder (nylon powder), polyethylene powder, polystyrene powder, polyethylene tetrafluoride powder and the like, inorganic white pigments (e.g., titanium dioxide, zinc oxide and the like); inorganic red series pigments (e.g., iron oxide (red iron oxide), iron titanate and the like); inorganic brown series pigments (e.g., gamma-iron oxide and the like); inorganic yellow series pigments (e.g., yellow iron oxide, bess and the like); inorganic black series pigments (e.g., black iron oxide, lower titanium oxide and the like); inorganic purple series pigments (e.g., mangoviolet, cobalt-violet and the like); inorganic green series pigments (e.g., chromium oxide, chromium hydroxide, cobalt titanate and the like; inorganic blue series pigments (e.g., ultramarine, Prussian blue and the like); pearl pigments (e.g., titanium oxide-coated mica, titanium oxide-coated bismuth oxychloride, titanium oxide-coated talc, colored titanium oxide-coated mica, bismuth oxychloride, fish scale flake and the like); metal powder pigments (e.g., aluminum powder, copper powder) and the like.

Examples of waxes include beeswax, candelilla wax, cotton wax, carnauba wax, bayberry wax, insect wax, spermaceti, montan wax, bran wax, kapok wax, lanolin acetate, liquid lanolin, sugarcane wax, lanolin fatty acid isopropyl, hexyl laurate, jojoba wax, shellac wax, and the like. If a wax is present, in an embodiment, it is present in amounts ranging from about 0.5% to about 2% by weight of the pharmaceutical composition, and in another embodiment, from about 1 to about 1.5% by weight of the pharmaceutical composition.

Examples of the hydrocarbon oil include liquid paraffin, ozokerite, squalane, pristane, and paraffin, ceresin, squalene, vaseline, microcrystalline wax and the like.

Examples of the higher fatty acid include lauric acid, myristic acid, palmitic acid, stearic acid, behenic acid, acid, tabic acid, isostearic acid, and the like.

Examples of the higher alcohols include straight alcohols (e.g., lauryl alcohol, cetyl alcohol, stearyl alcohol, myristyl alcohol, cetostearyl alcohol and the like); branched alcohols (e.g., monostearylglycerin ether (batyl alcohol), 2-decyltetradecinol, hexyldodecanol, isostearyl alcohol, octyldodecanol and the like) and the like.

Examples of the synthetic ester oil include isopropyl myristate, cetyl octanoate, octyldodecyl myristate, isopropyl palmitate, butyl stearate, hexyl laurate, myristyl myristate, hexyldecyl dimethyloctanoate, cetyl lactate, myristyl lactate, isocetyl stearate, isocetyl isostearate, di-2-ethylhexanoic acid ethylene glycol, dipentaerythritol fatty acid ester, monoisostearic acid N-alkyl glycol, dicapric acid neopentyl glycol, diisostearyl malate, di-2-heptylundecanoic acid glycerin, tri-2-ethylhexanoic acid trimethylolpropane, triisostearic acid trimethylolpropane, tetra-2-ethylhexanoic acid pentaerythritol, tri-2-ethylhexanoic acid glycerin, trioctanoic acid glycerin, triisopalmitic acid glycerin, triisostearic acid trimethylolpropane, cetyl 2-ethylhexanoate, 2-ethylhexyl palmitate, trimyristic acid glycerin, tri-2-heptylundecanoic acid glyceride, acetoglyceride, 2-heptylundecyl palmitate, diisobutyl adipate, N-lauroyl-L-glutamic hhacid-2-octyldodecyl ester, di-2-heptylundecyl adipate, ethyl laurate, 2-hexyldecyl myristate, 2-hexyldecyl palmitate, 2-hexyldecyl adipate, diisopropyl sebacate, 2-ethylhexyl succinate, triethyl citrate and the like.

Examples of skin humecants are aloe extract, urea, 1,3-butyleneglycol, glycerin, propylene glycol, sodium pyrrolidone carboxylate, and the like.

Examples of thickeners include gum Arabic, carrageenan, karaka gum, tragacanth gum, carob gum, quinceseed (*Cydonia oblonga*), caseine, dextrin, gelatin, sodium pectinate, sodium alginate, methylcellulose, ethylcellulose, CMC, hydroxyethylcellulose, hydroxypropylcellulose, PVA, PVM, PVP, sodium polyacrylate, carboxyvinyl polymer, amigel, locust bean gum, guar gum, tamarind gum, dialkyldimethylammonium sulfate cellulose, xanthan gum, aluminium magnesium silicate, bentonite, hectorite, AlMg silicate (Veegum), laponite amigel, anhydrous silicic acid and the like. If present, it is present in gelling effective amounts. In an embodiment, it is present, it is present from about 0.25% by weight to about 1.25% by weight.

Examples of ultraviolet absorbing agents include benzoic acid series ultraviolet absorbing agents (e.g., paraminobenzoic acid (hereinafter, abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester and the like); anthranilic acid series ultraviolet absorbing agents (e.g., homomethyl-N-acetyl anthranilate and the like); salicylic acid series ultraviolet absorbing agents (e.g., amyl salicylate, menthyl salicylate, homomethyl salicylate, octyl salicylate, phenyl salicylate, benzyl salicylate, p-isopropanol phenyl salicylate and the like); sinnamic acid series ultraviolet absorbing agents (e.g., octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-alpha-cyano-beta-phenyl cinnamate, 2-ethylhexyl-alpha-cyano-beta-phenyl cinnamate, glyceryl mono-2-ethylhexanoyl-diparamethoxy cinnamate and the like); benzophenone series ultraviolet absorbing agents (e.g., 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone and the like); 3-(4'-methylbenzylidene)-d,l-camphor, 3-benzylidene-d,l-camphor; 2-phenyl-5-methylbenzoxazole; 2,2'-hydroxy-5-methylphenylbenzotriazole; 2-(2'-hydroxy-5'-t-octylphenyl) benzotriazole; 2-(2'-hydroxy-5'-methylphenylbenzotriazole; dibenzaladine; dianisoylmethane; 4-methoxy-4'-t-butyldibenzoylmethane; 5-(3,3-dimethyl-2-norbornylidene)-3-pentane-2-one and the like.

Examples of sequestering agents include 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium methaphosphate, gluconic acid, phosphoric acid, citric acid, ascorbic acid, succinic acid, edetic acid, trisodium ethylenediaminehydroxyethyltriacetate, EDTA, or salt thereof, and the like. If present, it is present in less than about 1% by weight of the pharmaceutical composition.

Examples of lower alcohol include ethanol, propanol, isopropanol, isobutyl alcohol, t-butyl alcohol and the like.

Examples of polyols include diols (e.g., ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol and the like); triols (e.g., glycerin trimethylolpropane and the like); tetraols (e.g., pentaerythritol such as 1,2,6-hexanetriol and the like); pentaols (e.g., xylitol and the like); hexaols (sorbitol, mannitol and the like); polyol polymers (e.g., diethylene glycol, dipropylene glycol, triethylene glycol, polypropylene glycol, tetraethylene glycol, diglycerin, polyethylene glycol, triglycerin, tetraglycerin, polyglycerin and the like); diol alkyl ethers (e.g., ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether and the like); diol alkyl ethers (e.g., diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether and the like); diol ether ester (e.g., ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate and the like); glycerin monoalkyl ether (e.g., chimyl alcohol, selachyl alcohol, batyl alcohol and the like); glyceride; tetrahydrofurfuryl alcohol; POE-tetrahydrofurfuryl alcohol; POP-butyl ether; POP.POE-butyl ether; tripolyoxypropylene glycerin ether; POP-glycerin ether; POP-glycerin ether phosphoric acid; POP.POE-pentaerythritol ether, polyglycerin and the like.

Another optional ingredient is a skin protectant. A skin protectant agent is an agent which protects injured or exposed skin or mucous membrane surfaces from harmful or annoying stimuli and includes, but is not limited to, allantoin, calamine, cocoa butter, dimethicone, glycerin, kaolin, petrolatum, shark liver oil, silicates, silicas, protectant clays, zinc acetate, zinc carbonate, and zinc oxide. Skin protectant agents are well known in the art. One of ordinary skill in the art would understand, appreciate and recognize agents that are considered to be skin protectant agents. An extensive list of skin protectant agents can be found in the International Cosmetic Ingredient Dictionary and Handbook published by the Cosmetic, Toiletry, and Fragrance Association, Inc., under the listing "Skin Protectants," (herein incorporated by reference). If present, it is present in skin protectant amounts. In an embodiment, it is present in amounts ranging from about 0.1 to about 1% by weight, and in another embodiment, from about 0.4 to about 0.7 weight percent of the pharmaceutical composition.

The present pharmaceutical composition may optionally contain preservatives typically used in pharmaceutical and cosmetic compositions. Examples include methyl paraben, butyl paraben, ethyl paraben, sorbic acid, sodium benzoate, and the like. The pharmaceutical composition may additionally contain other microbicides. Examples include lauricidin and Merguard 1200. Additional preservatives or microbicides, if present, range from about 1% to about 9% by weight, and more preferably from about 4% to about 7% by weight of the pharmaceutical composition.

The pharmaceutical composition has a pH less than 3.5. In an embodiment, the pH ranges from about 2.0 to about 3.5. In another embodiment, the pH range from about 3.0 to about 3.3.

The pH of the composition does not require pH adjusting agents, however, buffers can be utilized to maintain the pH in the ranges described hereinabove.

The specific gravity of the composition is greater than about 0.9 and less than about 1.1. In an embodiment, it is greater than about 0.95 and in another embodiment, it ranges from about 0.95 to about 1.05.

The present pharmaceutical composition contains water. The amount of water present varies, but typically it contains at least about 60% by weight water. In an embodiment, it contains about 50 to about 70% water and in another embodiment, from about 57 to about 62% water.

In an embodiment, the pharmaceutical composition is comprised of a povidone-iodine complex having from about 8% to about 12% available iodine by weight in an amount ranging from about 1% to about 15% of the pharmaceutical composition. It contains one or more non-ionic surfactants and at least one quaternary ammonium surfactant in emulsifying effective amounts. It also contains coconut oil in the amount described herein. Further, it contains a tertiary amide in film forming effective amounts. In addition, it optionally contains beeswax. Furthermore, it optionally contains one or more of the following: a skin humectant, e.g., pyrrolidone carboxylic acid; a metal chelating agent, such as a metal EDTA, e.g., sodium or potassium EDTA; povidone; a neutraling organic base, such as trolamine; a preservative, such as polyquaternium 7, and/or lauricidin and/or Merguard 1200; a skin protectant, such as allantoin; a non-ionic detergent, such as Nonoxynol NP-9; a thickener such as sclerotium gum; process aid such as propylene glycol; and the like.

In another embodiment, the composition contains povidone-iodine in microbicidal effective amounts; tertiary amide in film forming effective amounts; at least one quaternary and at least one non-ionic surfactant in emulsifying effective amounts; coconut oil in the amount described hereinabove, and optionally beeswax in film forming effective amounts; and optionally at least one of the following: a metal chelating agent in a chelating effective amount, e.g., a skin humectant in an humectant effective amount; a skin protectant in a skin protectant effective amount; an organic base in acid neutralizing effective amounts; a non-ionic detergent in effective amounts; a thickener in gelling effective amounts; and/or additional microcides (such as preservatives). In another embodiment, it contains all of the aforementioned optional components in addition to the povidone iodine, surfactants and coconut oil.

In still another embodiment, the pharmaceutical composition contains povidone-iodine having from about 8% to about 12% available iodine by weight in an amount ranging from about 5 to about 15% by weight of the composition. It contains from about 0.1 to about 0.5% pyrrolidone carboxylic acid (a skin humectant), about 0.5 to 1.0% of a chelating agent, such as tetra sodium EDTA, about 1.5% to about 2.5% of additional povidone, from about 1.0% to about 1.5% of allantoin (a skin protectant active ingredient), about 0.3 to about 1.3% trolamine (a neutralizing organic base), from about 3.0% to about 4% of Merquat 550 (a preservative), which is polyquaternium 7, available from Calgon, and it is the polymeric quaternary ammonium salt consisting of acrylamide and dimethyl diallyl ammonium chloride monomers (dimethyl diallyl ammonium chloride acrylamide polymer), about 1.0 to about 7.0% by weight of Nonoxynol NP-9 (a nonionic detergent), about 7.5 to about 8.5% Triton X-100 (a nonionic detergent), which is a polyethylene glycol of p-(1, 1,3,3-tetra methyl butylphenylether), about 0.5 to about 2.5% amigel (sclerotium gum, a thickener at low pH), about 0.95% to about 1.5% of propylene glycol (a process aid), about 3.3 to about 5.0% Arosurf TA-100 (a quaternary surfactant), which is a softener and is dimethyldioctyldecyl ammonium chloride, about 1 to about 2% benzethonium steramide, about 0.5 to about 1%, cetyl stearate, about 0.2 to about 0.6% Merguard 1200 (a mixture of 2-bromo-2-bromethyl pentane-2,5-dinitrile with 2-phenoxy ethanol), about 2.5 to about 4.0% beeswax (an occlusive film former), about 2.0% to about 3% virgin coconut oil (a process aid) and about 10% to about 13% lauricidin (a preservative).

Suitable dosage forms include creams, ointments, lotions, gels, soap powder, spray, aerosols or any one of variety of topical forms for use in the topical administration of drugs.

The topical pharmaceutical composition of the present invention can also be made in any of formulations suitable for topical administration. Ointments, as is well known in the art of pharmaceutical formulation, are semisolid preparations that are typically based on petrolatum or other petroleum derivatives. The specific ointment foundation to be used, as will be appreciated by those skilled in the art, is one that will provide for optimum drug delivery, and, preferably, will provide for other desired characteristics as well, e.g., emolliency or the like. In general, ointment foundations may be grouped into four classes: oleaginous, emulsifiable, emulsion, and water-soluble. Oleaginous ointment foundations include, for example, vegetable oils, fats obtained from animals, and semisolid hydrocarbons obtained from petroleum. Emulsifiable ointment foundations, also known as absorbent ointment foundations, contain little or no water and include, for example, hydroxystearin sulfate, anhydrous lanolin and hydrophilic petrolatum. Emulsion ointment foundations are either water-in-oil (W/O) emulsions or oil-in-water (O/W) emulsions, and include, for example, cetyl alcohol, glyceryl monostearate, lanolin and stearic acid.

Creams, as also well known in the art, are viscous liquids or semisolid emulsions, either oil-in-water or water-in-oil. Cream foundations are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also contain an alcohol and, optionally, an oil. The gelling agents may be crosslinked acrylic acid polymers such as the "carbomer" family of polymers, e.g., carboxypolyalkylenes that may be obtained commercially under the Carbopol™. Also the hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin and amigel are preferred gels. In order to prepare a uniform gel, dispersing agents such as alcohol or glycerin can be added, or the gelling agent can be dispersed by trituration, mechanical mixing or stirring, or combinations thereof.

Lotions are preparations to be applied to the skin surface without friction, and are typically liquid or semiliquid preparations in which solid particles, including the active agent, are present in a water or alcohol base. Lotions are usually suspensions of solids that comprise a liquid oily emulsion of the oil-in-water type. Lotions can be used to treat large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable foundation. Depending on the nature of the foundation, pastes are divided between fatty pastes or those made from single-phase, aqueous gels. The foundation in a fatty paste is generally petrolatum or hydrophilic petrolatum or the like. The pastes made from single-phase aqueous gels generally incorporate carboxymethylcellulose or the like as the foundation.

The drug delivery system may be propelled by either pump or the use of propellants, such as hydrocarbons, hydrofluorocarbons, nitrogen, nitrous oxide, carbon dioxide or ethers, for example, dimethyl ether. In an embodiment, the gas is oxygen free. The drug delivery system is preferably in a single phase system as this allows less complicated manufacture.

A further embodiment is made when the pharmaceutical composition is packed in an aerosol can with instructions to shake before using. When shaken, there is separation in the can because of the gas, but it is not visible because the can is opaque. Shaking temporarily eliminates the separation. The gassy creme spreads easily.

Various additional delivery systems can be utilized, depending on the end use. An embodiment for hand sanitizing is a bag-in-box or wall mounted dispenser. Pump containers and tubes may also be utilized. For wound antiseptic use, an aerosolized can or a bag-on-valve (BOV) can may also be utilized. This permits antiseptic to be pushed into the wound. In another embodiment for hand delivery is a unit dose that allows complete coverage economically.

The composition is substantially free of any ingredient that reacts with iodine. By substantially free, that is meant that the composition contains less than about 10% by weight of a particular ingredient in the composition that is reactive with iodine, and more preferably less than about 5% by weight of the composition and even more preferably less than about 2% by weight and most preferably less than 1% by weight. Examples of components which are excluded which the composition is substantially free includes compounds containing carbon-carbon double bonds, except if as if the compound is aromatic and the only carbon-carbon double bond are within the aromatic ring or conjugated to the aromatic ring. In addition, the composition is substantially free of carbohydrates and other compounds which can form keto-enols. Further, the present composition is substantially free of anti-oxidants, organic perfumes and vitamins, proteins and amino acids.

The formulations of the present invention are prepared by art recognized techniques. Typically, the tertiary amide is prepared in situ, although it is not necessary, and it can be added to the other components. The tertiary amide or the hydrate is prepared in accordance with the procedure described in U.S. Patent Publication No. 2004/0122115, the contents of which are incorporated by reference. In one embodiment, the fatty acid is reacted with a quaternary ammonium cation in water under conditions to effect formation of the tertiary amide or hydrate thereof. Preferably, the reaction is conducted with an excess of fatty acid so that all of the quaternary ammonium cation is reacted to form the tertiary amide.

The tertiary amide may be separated from the reaction. Alternatively, the surfactants and coconut oil (or emulsifier mixture, as described hereinabove) and any other ingredient except povidone iodine are mixed together to form a homogenous mixture. Water is added and then povidone iodine is typically added last with gentle heating, slightly above room temperature. In an embodiment, it is heated at temperatures ranging from about room temperature to about 50° C., in another embodiment, from about 30° C. to about 45° C. until a homogenous mixture is formed.

The present composition is quite stable. It has a shelf-life of at least 24 months.

The present composition is useful as an antiseptic. It kills microorganisms, including microbes, bacteria, fungi, virus and mold. It is used to kill microorganisms on the skin.

An aliquot comprising a microbicidal effective amount of the pharmaceutical composition is placed on the area of the skin to fully cover the area of the skin of the mammal which is to be cleansed from microbes. In an embodiment, at least about 0.01 g per square inch of the pharmaceutical composition is placed on to the area on the skin where the composition is to be applied, e.g., on the hands of the subject. In another embodiment, 0.01 g to about 0.03 g per square inch of the pharmaceutical composition is applied to the area of the skin being cleansed of microbes. In another embodiment, 0.01 g to 1 gm per square inch is utilized. Excess amounts of the pharmaceutical composition can be used, for the excess amount is washed off, as described hereinbelow. The pharmaceutical composition is spread across all surfaces of the skin area so that the area to be cleansed from the microbes is completely covered with the pharmaceutical composition. If it is the hands or feet that are to be cleansed, for example, it is spread across all surfaces of the hands or feet, including under the nails, cuticles, fingertips (or tips of the digits) and wrists (or ankles). The composition is rubbed briskly until dry. After all areas of the area to be cleansed of microbes has been covered with the pharmaceutical composition, the composition is allowed to remain on the skin for sufficient time to kill the microbes thereon. In an embodiment, the composition remains on the skin for at least 30 seconds and in another embodiment, for at least 120 seconds. In an embodiment, it remains on the skin for about 30 seconds to about 5 minutes, and in another embodiment, it remains on the skin for about 45 seconds to about 2 minutes. Then it is rinsed off with water.

Although it can be used as often as one wants, the composition is effective against various microbes for about 6 hours, at which time, the process is repeated again. The composition may be applied externally to all parts of the body, although it is not to be ingested or placed in someone's eye or ear.

Besides killing microbes, the product is also effective in healing cuts, wounds or open sores on the body. Again, the treatment regimen is as before, except that the microbicidal effective amount of the composition is applied directly to the wound to be treated. The microbial effective amount in this utility is the same as a microbicidal effective amount as an antiseptic.

After a time sufficient to kill microbes, for example, 20 minutes, the residue is rinsed from the wound. This is applied each time the wound is dressed until the wound is healed. In an embodiment, this is about 7 times per week to about one time per week.

Optimal amounts and the regimen of treatment may readily be determined by those skilled in the art and will vary with the particular composition used, the strength of the preparation, the severity of the wound or sore. In addition, factors associated with the particular subjects being treated, including the subject age, weight, diet and time of administration will result in the need to adjust the amount and regimen to appropriate therapeutic levels, which can easily be determined by the physician.

Without wishing to be bound, it is believed that the mechanism of action is as follows:

1. The crème is rich in nonionic surfactants.
2. As the product is mixed during cooking, air is incorporated into the mix.
3. The surfactants migrate to the gas/liquid interface, creating a multitude of bubbles. More small bubbles (foam) increase the surface area.
4. Dissolved iodine is heavier than water and visibly (strong purple color) migrates to the gas/liquid interface.
5. The bubble becomes lined with high density, iodine-in-water.
6. When bubbles coalesce during storage and distribution, iodine water accumulates until a critical mass is reached.
7. The critical mass of iodine water then forms "creeks, rivers and then lakes". Lakes are visible to the naked eye as pools of purple and are described as visible phase separation.
8. When coconut oil is mixed into the crème, the surfactant surrounds the oil to try and emulsify it, reducing the amount of surfactant available at the bubble interface and making small bubbles into large bubbles with less macro surface area.
9. The crème is now a "chocolate pudding-like" gel.
10. By pulling a vacuum, the bubble interface is removed mechanically. There is no gas/no gas interface. The specific gravity increases to 1.0 from 0.92.
11. The product remains phase stable.
12. The low pH makes the product chemically stable.
13. The coconut oil breaks the gel by removing surfactant from the gel as the surfactants try to emulsify the fat, so the crème can release the gas. The heavy crème flows easily and spreads evenly.

It is believed that the fat globules are surrounded by nonionic detergents much like a dandelion flower that has gone to seed. As rub-in progresses, the surfactant-surrounded-fat goes to the skin. The short chain fats ($C_{8-12}$) are absorbed by the skin; the surrounding detergent is released to find soils and microbes on the skin and lift them off the skin. The surfactants are not absorbed. The long chain fats ($C_{\geq 16}$) are rejected by the skin and mix with the povidone, and beeswax, if present or other softener to form a silky smooth occlusive layer over the skin. This layer keeps inside moisture in and outside moisture out. The skin stays hydrated; environmental insults are blocked.

The tertiary amide is believed to form a tertiary amide acid hydrate [$(TA)_3.H_3O+$] with a central positive charge. During rub-in, the positive charges of the hydrate compounds separate the hydrates uniformly over the skin. The negative charge of the skin attracts the uniform, positive hydrate film. The fatty acid tail of the hydrate penetrates the stratum corneum (SC) until the electrostatic attraction is balanced by the resistance through the SC. A positively-charged fatty layer deposits over the entire skin and is mechanically attached to the SC.

The short chain fats migrate through this film into the dermis. In the dermis, the body converts fats into fatty acids. The new fatty acids reduce the local blood pH. The circulating hemoglobin releases lowered-pH-Bohr-Effect oxygen locally and skin health is stimulated by the increased oxygen availability. Damaged skin recovers and pre-existing "safe harbor" cracks in the skin heal. The hands are more resistant to colonization by eliminating safe harbors.

Meanwhile, unreacted cationic surfactants emulsify wax, long chain fats and povidone to form a positively-charged occlusive layer. This layer is the last-to-dry and is electrostatically repelled by the acid hydrate film. Between these two films is a layer of "peanut butter and jelly" made from preservatives and nonionic detergents. After drying, excess preservative and detergent is rinsed away, assuring a persistent, reproducible layer captured between the proximal acid hydrate film and the distal cationic waxy film. The addition of the long chain fats from the coconut oil provides the distal film with a cosmetically elegant hand feel after rinsing and drying. The sandwich makes the crème's antimicrobial activity persistent for about 6 hours or until the old skin is sloughed off. Sloughing old skin discards the sandwich.

The following non limiting examples further illustrate the present invention.

EXAMPLE 1

The topical composition contains the following raw materials in grams:

| Raw Material | Target Usage |
| --- | --- |
| LAURICIDIN | 717 |
| VIRGIN COCONUT OIL | 160 |
| CRUDE BEESWAX | 207 |
| STEARIC ACID | 668 |
| BENZETHONIUM Cl | 103 |
| MERGUARD 1200 | 29 |
| CETYL ALCOHOL | 589 |
| AROSURF TA-100 | 268 |
| PROPYLENE GLYCOL | 717 |
| AMIGEL | 120 |
| TRITON X-100 | 509 |
| NONOXYNOL NP-9 | 405 |
| MERQUAT 550 | 225 |
| TROLAMINE | 80 |
| ALLANTOIN | 88 |
| POVIDONE | 120 |
| TETRA SODIUM EDTA | 48 |
| PCA | 19 |
| POVIDONE IODINE | 1,200 |
| WATER | 0.5 |

36.5 grams water was added to a kettle with stearic acid and benzethonium chloride. It is heated with gentle stirring to 70°-85° C. for about 15 minutes to form benzethonium stearamide. Then cetyl alcohol is added to the kettle, and the product is mixed for another 35 minuets at the same temperature to form additional benzethonium stearamide and cetyl stearate. Triton X-100, NP-9 and Merquat 550, TEA, Arosurf TA-100, povidone, EDTA and PCA (Povidone carboxylic acid), Lauricidin, beeswax and coconut oil are added to the kettle and the components are mixed until homogenous. The heater is turned off. When it cools, allantoin is added and mixed together. Then propylene glycol and Amigel are added at 70° C.; then at 64° C., water is added all at once @ QS to make 16,000 grams (total batch weight). Finally, Povidone iodine is added, and mixing is continued until the temperature falls to 44° C. A vacuum is pulled on the batch for a time sufficient to increase the specific gravity to 0.92 to 1.02. Specific gravity is tested by taking a small jar of crème and weighing the net weight of crème divided by the net weight of pure water in the same type jar. The vacuum can be pulled either in the mixing kettle or in a work-in-progress holding vessel.

COMPARATIVE EXAMPLE 1

A pharmaceutical composition was made according to Example 1, except the vacuum step was eliminated. The pH was 3.1; the specific gravity was 0.87. This product was chemically stable, but not physically stable.

COMPARATIVE EXAMPLE 2

The pharmaceutical composition was prepared according to the procedure in Example 1, except that TEA is 0.71% and there was no coconut oil present. Further, the specific gravity was 0.87. The pH of the pharmaceutical composition was 3.65. The shelf life was 16 months.

Shelf life was determined by the following methods: The level of povidone iodine in the pharmaceutical composition is tested periodically. When the concentration falls to the minimum acceptable level, for example, 5% povidone-iodine, the product is no longer considered to be sold, and the shelf life is determined. Alternatively, the phase stability is determined by packing the composition in a clear container. Deep purple iodine-water is observed at the base of the container if the product is unstable. Whichever test fails first determines the composition's shelf life. Standardized accelerated tests are used, for example, storing @ 40° C. to predict ambient shelf life. These techniques are well known to skilled artisans.

EXAMPLE 2

A pharmaceutical composition was made according to Example 1. The pH was 3.06; the specific gravity was 1.02. The product was chemically and physically stable for 24 months, using the procedure in Comparative Example 2.

EXAMPLE 3

Effects of the Formulation of EX 1 Protocol on Hospital Acquired *Clostridium Difficile* Infections and Employee Absenteeism Purpose:

This study is designed to evaluate the efficacy and clinical acceptance of a hand sanitizer protocol using the formulation of Ex 1. The outcomes to be determined are the effects of the composition on the rate of facility acquired *Clostridium difficile* (*C. diff.*) and MRSA infections and employee absentee rate.

Methods:

Employees of the long-term care facility are provided a single 15 minute in-service to educate them and to demonstrate the application of the topical composition of Ex 1. They are instructed to apply the composition at the beginning of their shifts, every six hours while at work and before they leave the facility at the end of their shifts. They are instructed to follow the same CDC guidelines for hand hygiene between applications of the composition as they had been following prior to the introduction of the Protocol. The rates of facility acquired *Clostridium difficile* and MRSA during a 4 month study interval are being compared to historical records of *C. diff.* and MRSA infections from the 7 months preceding the study for which records are made available. The effect of the pharmaceutical composition on employee absenteeism will be evaluated by comparing the rates during this 4 month trial to the historical rates from the same 4 month intervals in the two preceding years. No other hygienic interventions or procedural changes are to occur during the study interval.

Employee absences from the acute care floor where the Protocol is originally initiated are compared to the same time intervals in the two prior years.

Discussion

Approximately 1 of every 10 hospitalized patients will acquire an infection after admission resulting in substantial costs to the healthcare system. In 2002, the cost was estimated to be $6.7 billion in the United States. Due to the enormous costs and devastating health impacts of these infections, a great deal of attention has been focused on their prevention. The most important process in preventing these infections is proper hand hygiene between patient contacts. Numerous studies have been performed demonstrating the reduction in facility acquired infections when proper hand hygiene is practiced. Despite the fact that most healthcare facilities have adopted the CDC guidelines for hand hygiene, adherence to this by healthcare personnel has remained low with the average rate of compliance being approximately 40%. Explanations for poor hand hygiene compliance by healthcare personnel are numerous and demonstrate obvious areas for improvement in the current science of hand sanitizers and hand hygiene protocols.

TABLE 1

| Self-reported factors for poor adherence with hand hygiene | Additional perceived barriers to appropriate hand hygiene |
| --- | --- |
| Handwashing agents cause irritation and dryness | Lack of active participation in hand-hygiene promotion at individual or institutional level |
| Sinks are inconveniently located/shortage of sinks | Lack of role model for hand hygiene |
| Lack of soap and paper towels | Lack of institutional priority for hand hygiene |
| Often too busy/insufficient time | |
| Understaffing/overcrowding | Lack of administrative sanction of noncompliers/rewarding compliers |
| Patient needs take priority | |
| Hand hygiene interferes with health-care worker relationships with patients | Lack of institutional safety climate |
| Low risk of acquiring infection from patients | |
| Wearing of gloves/beliefs that glove use obviates the need for hand hygiene | |
| Lack of knowledge of guidelines/protocols | |
| Not thinking about it/forgetfulness | |
| No role model from colleagues or superiors | |

TABLE 1-continued

| Self-reported factors for poor adherence with hand hygiene | Additional perceived barriers to appropriate hand hygiene |
|---|---|
| Skepticism regarding the value of hand hygiene | |
| Disagreement with the recommendations | |
| Lack of scientific information of definitive impact of improved hand hygiene on health-care-associated infection rates | |

* Source: Adapted from Pittet D. Improving compliance with hand hygiene in hospitals. Infect Control Hosp Epidemiol 2000; 21: 381-6.

Additionally, none of the agents in any currently available hand antiseptic products demonstrate any reliable activity against spore forming bacteria such as *Clostridium difficile* and *Bacillus anthracis*. Reliable activity against *Clostridium difficile* is important because it can be cultured from the hands of 60% of physicians and nurses caring for patients with these infections. Poor hand hygiene and unreliable activity of hand sanitizers against *C. diff.* have resulted in the rapid growth and widespread occurrence of healthcare associated diarrhea caused by this organism which creates significantly negative health impacts on patients and staff. The rapid growth of *C. diff.* infections has earned it the recent distinction as "the new superbug on the rise in hospitals."

However, it is expected that adherence to the protocol using the pharmaceutical composition of the present invention, such as the composition of Example 1, reduces dramatically the presence of *clostridium difficle* and other microorganisms.

Unless indicated to the contrary, lower alkyl as used herein refers to alkyl group containing 1-6 carbon atoms.

The plural denotes the singular and vice versa.

"Preventing", "prevention", "suppress", "suppressing" and "suppression" as used herein refer to administering the composition of the present disclosure after the initial application of the pharmaceutical composition to the area being cleansed of microbes and prevents and/or decreases the probability of infection of microbes and/or any symptom, aspect or characteristic of the microbial infection in the area on the skin of the subject to which the composition of the present invention has been applied. Such preventing and suppressing need not be absolute to be useful.

The terms "treat", "treating" and "treatment", as used herein, refers to administering the composition of the present disclosure after the cutaneous injury or appearance of a wound or open sore so as to reduce or eliminate any symptom, aspect or characteristic of the condition associated with the wound or sore. In one embodiment, the treatment provides healing of the wound or sore. Such treating need not be absolute to be useful.

As used herein, the term "in need of treatment" as used herein refers to a judgment made by a caregiver that a patient requires or will benefit from treatment. This judgment is made based on a variety of factors that are in the realm of a caregiver's expertise.

As used herein, the term "in need of prevention" as used herein refers to a judgment made by a caregiver that a patient requires or will benefit from prevention. This judgment is made based on a variety of factors that are in the realm of a caregiver's expertise.

As used herein, the terms "subject", "individual" or "patient" refers to any mammal, such as, but not limited to, mice, rats, other rodents, rabbits, dogs, cats, swine, cattle, sheep, horses, or primates, or humans. The term may specify male, female, or both, or exclude male or female. Preferred subjects are humans.

As used herein, the term "therapeutically effective amount", in reference to the treating, preventing or suppressing of a disease state/condition, refers to an amount of a composition either alone or as contained in a pharmaceutical composition that is capable of having any detectable, positive effect on any symptom, aspect, or characteristics of the disease state/condition. Such effect need not be absolute to be beneficial.

Unless indicated to the contrary, all weight percentage is by dry weight of the pharmaceutical composition.

As used herein, the term "topical administration" is used in its conventional sense to mean delivery of a drug or pharmacologically active agent to the skin or mucosa, as in, for example, the treatment of various skin disorders. In general, topical administration provides a local effect.

The above preferred embodiment, and example was given to illustrate the scope and spirit of the present invention. These embodiments and examples will make apparent to those skilled in the art other embodiments and examples.

What is claimed is:

1. A method for treating a wound or open sore on a subject which comprises
placing a microbicidal effective amount of a topical pharmaceutical composition onto the wound or open sore and rubbing the composition thereon thoroughly,
said composition comprising:
an antiseptic effective amount of povidone-iodine complex wherein the amount of complexed iodine in the povidone-iodine complex is from about 4% to about 12% by weight of the povidone-iodine complex;
a second component comprising a tertiary amide or a salt thereof or a hydrate thereof, said second component present in an amount from about 0.1% to about 2% by weight of the composition;
coconut oil in an amount from about 0.5% to about 2% by weight of the composition;
an emulsifying effective amount of a surfactant; and water;
said composition having a pH of about 2.0 to about 3.5 and having a specific gravity from about 0.9 to about 1.1; and
said composition containing less than 5% by weight of an ingredient that reacts with iodine.

2. The method according to claim 1, wherein the povidone-iodine complex is present in an amount from about 5% to about 10% by weight of the composition.

3. The method according to claim 1, wherein the surfactant is a polyethylene glycol of 4-(1,1,3,3-tetramethylbutyl)-phenyl, or Nonoxynol 9, or combination thereof.

4. The method according to claim 3, wherein the povidone-iodine complex is present in an amount from about 5% to about 10% by weight of the composition.

5. The method according to claim 1, wherein the composition further comprises beeswax.

6. The method according to claim 1, wherein the tertiary amide has the formula

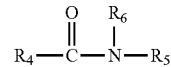

wherein $R_4$ is a saturated fatty group of 11-29 carbon atoms;
$R_5$ and $R_6$ are independently lower alkyl aryl, aryl lower alkyl, or saturated fatty group containing 11-29 carbon atoms or $R_7$:

R$_7$ is

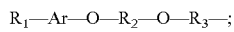
R$_1$—Ar—O—R$_2$—O—R$_3$—;

R$_2$ and R$_3$ are independently alkylene groups containing 1-6 carbon atoms,
R$_1$ is a lower alkyl, and
Ar is aryl.

7. The method according to claim 6, wherein R$_4$ is a saturated fatty group containing 15-21 carbon atoms.

8. The method according to claim 6, wherein R$_5$ is aryl or aryl lower alkyl; and R$_6$ is

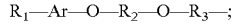
R$_1$—Ar—O—R$_2$—O—R$_3$—;

R$_2$ and R$_3$ are independently alkylene containing 1-3 carbon atoms; and Ar is aryl.

9. The method according to claim 6, wherein Ar is phenyl.

10. The method according to claim 6, wherein R$_5$ is aryl lower alkyl.

11. The method according to claim 6, wherein R$_5$ is benzyl.

12. The method according to claim 11, wherein R$_4$ is a saturated fatty group containing 15-21 carbon atoms.

13. The method according to claim 6, wherein the tertiary amide is benzethonium stearamide or benzalkonium stearamide.

14. The method according to claim 1, wherein the second component comprises a hydrate of a tertiary amide, wherein the tertiary amide is of the formula

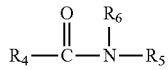

R$_4$ is a saturated fatty group of 11-29 carbon atoms;
R$_5$ and R$_6$ are independently lower alkyl, aryl, aryl lower alkyl, or fatty group containing 11-29 carbon atoms or R$_7$;
R$_7$ is

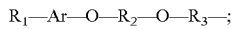
R$_1$—Ar—O—R$_2$—O—R$_3$—;

R$_2$ and R$_3$ are independently alkylene groups containing 1-6 carbon atoms;
R$_1$ is an alkyl group containing 1-15 carbon atoms; and
Ar is aryl.

15. The method according to claim 1, wherein the composition is in the form of a paste, cream or ointment.

16. The method according to claim 1, wherein the composition is in the form of an aerosol spray.

* * * * *